United States Patent [19]

Lebo, Jr.

[11] Patent Number: 5,529,772
[45] Date of Patent: Jun. 25, 1996

[54] METHOD FOR PRODUCING IMPROVED BIOLOGICAL PESTICIDES

[75] Inventor: Stuart E. Lebo, Jr., Schofield, Wis.

[73] Assignee: LignoTech, USA, Inc., Rothschild, Wis.

[21] Appl. No.: 257,658

[22] Filed: Jun. 9, 1994

[51] Int. Cl.$^6$ ............ A61K 7/42; A61K 31/70; C07G 1/00; C07K 1/107
[52] U.S. Cl. ............ 424/93.1; 424/59; 504/117; 514/22; 530/402; 530/500
[58] Field of Search ............ 424/93.1, 59; 514/22; 504/113, 117; 530/402, 500

[56] References Cited

U.S. PATENT DOCUMENTS

| Re. 29,238 | 5/1977 | Dimitri et al. | 71/101 |
|---|---|---|---|
| 2,090,109 | 8/1937 | Coe | 167/24 |
| 2,800,458 | 7/1957 | Green | 252/316 |
| 3,242,051 | 3/1966 | Hiestand et al. | 167/81 |
| 3,505,254 | 4/1970 | Kidwell et al. | 260/3 |
| 3,813,236 | 5/1974 | Allan | 71/94 |
| 3,839,561 | 10/1974 | Bordenca | 424/174 |
| 4,094,969 | 6/1978 | Batzer et al. | 424/78 |
| 4,184,866 | 1/1980 | DelliColli et al. | 71/65 |
| 4,244,728 | 1/1981 | DelliColli et al. | 71/65 |
| 4,244,729 | 1/1981 | DelliColli et al. | 71/65 |
| 4,280,833 | 6/1981 | Beestman et al. | 71/100 |
| 4,417,916 | 11/1983 | Beestman et al. | 71/93 |
| 4,844,896 | 7/1989 | Bohm et al. | 424/89 |
| 4,846,888 | 7/1989 | Detroit | 106/93 |
| 4,938,797 | 7/1990 | Hasslin et al. | 71/118 |

FOREIGN PATENT DOCUMENTS 0653158  5/1995  European Pat. Off. .
WO92/19102  11/1992  WIPO .

OTHER PUBLICATIONS

Martignoni et al, Laboratory Evaluation of New Ultraviolet Absorbers for Protection of Douglas–fir Tussock Moth (Lepidoptera: Lymantriidae) Baculovirus, Journal of Economic Entomology, 78, Aug. 1985.

Patent Abstracts of Japan, vol. 11, No. 349, C–456, abstract of JP, A, 62–120301 (Hokko Chem. Ind. Co. Ltd.), Jun. 1, 1987.

"What's New in the Ever–Changing World of Micro and Macroencapsulation", Suzanne Christiansen, Soap/Cosmetics/Chemical Specialties, Sep., 1992, pp. 26–28.

*Primary Examiner*—Douglas W. Robinson
*Assistant Examiner*—Elizabeth F. McElwain
*Attorney, Agent, or Firm*—Andrus, Sceales, Starke & Sawall

[57] ABSTRACT

A method for producing agriculturally active substances such as pesticides to provide improved resistance to environmental degradation, especially heat and ultra-violet light. The method involves the direct reaction of an active protein toxin of a biologically derived pesticide with a UV protectant to form a stable complex having the UV protectant as an integral part of its structure. The method employs lignosulfonates, such as sulfite lignin or sulfonated lignin, or alternately sulfonated lignite, sulfonated tannins, napthalene sulfonates or other related compounds as the UV protectant.

19 Claims, No Drawings

METHOD FOR PRODUCING IMPROVED BIOLOGICAL PESTICIDES

BACKGROUND OF THE INVENTION

The present invention relates to a method for producing improved biological pesticides. Biological pesticides produced via the method have improved resistance to environmental degradation, especially that caused by exposure to ultra-violet (UV) light and/or heat. The method works particularly well for *Bacillus thuringiensis* toxin but can also be used to protect other toxins such as those produced by other Bacillus strains and by UV sensitive viruses and/or fungi.

The UV sensitivity of such biological pesticides is well known. By use of the process described herein, the UV sensitivity of the active toxins in such biopesticides can be greatly reduced.

A number of microencapsulation systems have been proposed for providing protection of agriculturally active substances.

One method suggested in U.S. Pat. No. 3,839,561 utilizes diisophorone derivatives to protect active cyclopropane carboxylic acid compounds from ultra-violet induced degradation. Similarly, U.S. Pat. No. 4,094,969 describes the use of a sulfonated copolymer of catechin and leucocyanidin as a UV stabilizer. In both cases, however, the formulations suggested do not maintain the sunscreen and active ingredient in close enough contact to be effective.

In U.S. Pat. No. 3,242,051, a method for coating materials by phase separation is described. Gelatin and various carboylated polymers such as gum acacia and ethyl cellulose are used to form the coating. The use of a similar ethylcellulose/gelatin system is described by Ignoffo and Batzer in "Microencapsulation and Ultraviolet Protectants to Increase Sunlight Stability of an Insect Virus", *J. Econ. Entomology*, Vol. 64, pp. 850–853 (1966), and the use of a chlorophyll green/gelatin system is described in U.S. Pat. No. 2,090,109. In these cases, however, the materials have less than desirable environmental stability. Another disadvantage of these polymers is that they are not always capable of keeping the sunscreening agent within the capsule wall.

Encapsulation of actives by interfacial polycondensation is described in U.S. Pat. Nos. 4,280,833 and 4,417,916. The actives thus formed have a skin or thin wall of polyurea which improves release characteristics and environmental stability. In the process, lignin sulfonate is used as an emulsifier.

The use of lignin in controlled release of actives is also known in the prior art. The preparation of controlled release composites of lignin and biologically active materials is described in U.S. Pat. No. 3,929,453 (Re. 29,238). The composites described are obtained by coprecipitation-inclusion from an aqueous alkaline lignin solution, or by the elimination of a common solvent from a lignin-biologically active organic agent mixture. Preparation of reversibly swellable lignin gels is described in U.S. Pat. Nos. 4,184,866 and 4,244,729. The described gels are formed by crosslinking lignin with epichlorohydrin and are able to sustain the release of water-soluble and water-insoluble pesticides. The use of other crosslinking agents such as formaldehyde and glutaric dialdehyde is described in a related U.S. Pat. No. 4,244,728. The use of said gels for UV protection, however, is not disclosed in any of these patents.

The use of sunscreen agents in combination with encapsulation is described in U.S. Pat. No. 4,844,896. Suggested sunscreen agents include methyl orange, malachite green, methyl green and other colored dyes, and suggested encapsulating agents include Eudragit L, Eudragit S, polyacrylic acid and other polyacrylates. It is claimed that such systems keep the sunscreen agent within the capsule. Incorporation of the sunscreen into the capsule wall is not disclosed, however, and the problem of sunscreen catalyzed degradation is not addressed.

U.S. Pat. Nos. 4,844,896 and No. 4,948,586 describe methods for encapsulating insecticidal pathogens together with sunscreen agents in polyacrylate encapsulating agents. The sunscreens used include dyes such as methyl green and methyl orange (U.S. Pat. No. 4,844,896) and organic chemicals such as bezophenone and p-aminobenzoic acid (U.S. Pat. No. 4,948,586). Both of the methods described, however, are relatively complex and the sunscreens used are quite costly. A similarly described process using lignin as a sunscreen agent is described in International Application No. PCT/US92/03727. While the use of lignin reduces the cost of the sunscreen, the process involved is still complex and relatively costly.

In "Protection of *Bacillus Thuringiensis* from Inactivation by Sunlight", *Can. Ent.* 115, pp. 1215–1227 (1983), Morris examined the effects of addition of a number of varied sunscreening agents on the UV stability of commercially available *Bacillus thuringiensis* formulations. In "Photoprotection of *Bacillus thuringiensis kurstaki* from Ultraviolet Irradiation", *J. Invert. Path.*, 57, pp. 343–351 (1991), Cohen, et al conducted similar studies with cationic chromophores as the selected sunscreens. Margulies, et al in *Arch. Insect Biochem. Physiol.*, 22, pp. 467–486 (1993) reported the effects of cationic dyes and/or mixtures of cationic dyes and clays on the UV stability of biological and chemical pesticides. While increased protection was reported in all three studies, treatment costs were quite high.

The objective of this invention, on the other hand, is to react ultra-violet sunscreens, and more specifically sulfonated lignins, sulfonated lignites, naphthalene sulfonates, and other related compounds, directly with a protein toxin to form a stable complex. Chemical bonds keep the sunscreen agents from diffusing out of the complex where they are ineffective. A further objective of incorporation of the sunscreen directly with the toxin is to minimize sunscreen catalyzed degradation of sensitive actives.

Still another objective of the invention is to minimize the number of ingredients needed in the procedure, thereby simplifying the overall process and minimizing production costs.

Other objectives and advantages of the invention will become evident on reading the following detailed descriptions.

SUMMARY OF THE INVENTION

It is well known that under specific conditions sulfonated compounds such as lignins or tannins and carboxylated compounds such as modified lignins or natural gums react with proteins. In fact, the complexation of gelatin (a protein) and gum arabic is the basis for microencapsulation of many pharmaceutical materials. The complexes formed between proteins and sulfonated or carboxylated compounds have low solubility in acid systems. In alkaline systems, however, ionic interaction ceases and re-dissociation occurs.

It is also well known that sulfonated lignins derived from the sulfite pulping of wood or by sulfonation of lignins derived from Kraft pulping of wood, sulfonated lignites derived from the sulfonation of lignite coal, sulfonated tannins derived by the sulfonation of bark tannins, synthetically prepared naphthalene sulfonates and other related compounds are efficient absorbers of UV light. Phenolic, other aromatic, carbonyl, catecholic and carboxyl functionalities all contribute to the ability of these types of compounds to efficiently absorb UV light. Modifications such as high temperature and other types of oxidation and/or azo-coupling as described in U.S. Pat. No. 4,846,888 can significantly increase the UV light absorbing efficiency of these compounds particularly in the case of lignin sulfonates. Another advantage to the use of these compounds as UV absorbers is that they can effectively dissipate the energy associated with the absorption of UV light internally thereby preventing energy transfer to other proximate materials.

It is further known that the active toxin in many biopesticides is proteinacious in nature or contained in a protein matrix. For example, the active toxin of *Bacillus thuringiensis* is a protein crystal, the parasporal body. In the case of virus based biopesticides, the virus itself is contained in protein inclusion bodies.

In the present invention, the UV resistance of biopesticides is improved by the direct reaction of protein toxins with UV light absorbing compounds such as sulfonated lignins, sulfonated lignites, sulfonated tannins, naphthalene sulfonates, etc. When maintained at the proper pH, the complexes thus formed are stable and have improved resistance to UV light and/or heat induced degradation. When introduced into an alkaline system such as is present in the stomach of many of the insects such biologically derived toxins target, the complex decomposes and the toxins become active. The present invention also has the advantages of requiring minimum amounts of chemicals to produce, it is easy to use, relatively inexpensive, and the chemicals needed are non-toxic and environmentally safe.

DETAILED DESCRIPTION OF THE PREFERRED EMBODIMENT

It has been found that the UV sensitivity of biopesticide toxins or actives can be greatly reduced by the process described in this invention.

Such actives include any UV sensitive biologically derived pesticide. As used herein the term "pesticide" has its normal connotation, and is intended to encompass insecticides, herbicides, fungicides, rodenticides, molluscicides, miticides, ovicides, algicides, larvacides, bactericides, and nematocides. For example, the UV sensitive, agriculturally active agent might be a biologically derived pesticide such as a virus, a bacterium, a nematode or a fungus. Viruses include, but are not limited to, the nuclear polyhedrosis virus (NPV) of the bullworm, *Hellothis zea*, of the gypsy moth *Lymantria dispar*, of the Douglas fir tossock moth, *Orgia pseudotsugata*, of the European pine saw fly *Neodiprion sertifer* or of *Autographa californica* or of *H. virescens*. Bacteria known to be insecticidal agents, include but are not limited to *Bacilllus thuringienisis*, Bacillus Sphaericus, Bacillus Popilliae and Bacillus Cereus. Examples of possible nematodes include *Neoaplectana carpocapsae, Octomyomermis muspratti, Steinenema carpocapsae* and *Romanomermis culiciuora*. Examples of possible fungi include *Verticillum lecanii* and Entomophathora genus.

Any lignosulfonate, sulfonated lignite, sulfonated tannin or related compound such as napthalene sulfonates or condensed naphthalene sulfonates can be used as a UV protectant in the invention. These compounds are well known and are derived from the sulfite pulping of wood, by sulfonation of lignins derived from the kraft pulping of wood, by sulfonation of tannins derived from wood barks, etc. The lignin materials used are typically in the salt form (i.e. sodium, potassium, etc.) Preferable materials are those with high molecular weight, strong absorptivities in the 290–400 nm wavelength range and sufficient sulfonation to ensure efficient reaction with the proteinacious materials.

The lignosulfonates which may be utilized as the UV protectant materials in the practice of and to obtain the novel protein/UV protectant complex of the present invention are the treated or untreated spent sulfite liquors containing the desired effluent lignosulfonate solids obtained from wood conversion as the sulfite waste pulping liquor. These, as indicated, may be utilized in the "as is" or whole liquor condition. They may also be utilized as a purified lignosulfonate material from, or in which the sugars and other saccharide constituents have been removed and/or destroyed, or additionally inorganic constituents have been partially or fully eliminated. Also sulfonated or sulfoalkylated kraft lignin can be used as an adequate UV protectant material.

As used herein, the term "kraft lignin" has its normal connotation, and refers to the substance which is typically recovered from alkaline pulping black liquors such as are produced in the kraft, soda and other well known alkaline pulping operations. The term "sulfonated lignin", as used in the specification refers to the product which is obtained by the introduction of sulfonic acid groups into the kraft lignin molecule, as may be accomplished by reaction of the kraft lignin with sulfite or bisulfite compounds, so that kraft lignin is rendered soluble in water. As used herein, the term "sulfite lignin" refers to the reaction product of lignin which is inherently obtained during the sulfite pulping of wood, and is a principle constituent of spent sulfite liquor. The term "lignosulfonate" ($LSO_3$) encompasses not only the sulfite lignin, but also the sulfonated lignin herein above described. Any type of lignosulfonate that is hardwood, softwood, crude, or pure may be employed. Preferably, lignosulfonates in their as is or whole liquor condition are employed. For example calcium lignosulfonates, sodium lignosulfonates, ammonium lignosulfonates, modified lignosulfonates and mixtures or blends thereof may all be utilized herein. Lignosulfonates are available from numerous sources in either aqueous solution or dried powder forms. For example Lignotech USA, Inc. sells lignosulfonates under the trade designations Lignosol, Norlig, and Marasperse which are appropriate for use in the present invention. These are generally derived from sulfite waste pulping liquors with Marasperse being considerably refined as to sugars and certain inorganics contents compared to Norlig. The Lignosol products are derived from substantially softwood sulfite waste pulping liquors and can be whole liquor "as is" raw materials or, depending on processing, can be modified or purified softwood lignosulfonates.

As noted previously, napthalene sulfonates or condensed naphthalene sulfonates may also be used as the UV protectant. Naphthalene sulfonates are well known, and are typically synthesized via sulfonation of napthalene, and napthalene condensates.

In general, the lignosulfonates are anionic polyelectrolytes with a relative molecular size usually on the order of 1,000 to 20,000. They generally have an organic sulfonic sulfur, that is—$SO_3$, content calculated as percent sulfur by weight of broadly between about 0.5 to about 15 percent. More advantageously for many purposes, this sulfur range is between about 0.75 to about 10 percent. Quite often it is preferable for the lignosulfonate to contain from about 1.0 to 8 weight percent of the combined sulfur which represents its appearance in the sulfonic form.

In the invention, the UV protectant is dissolved in a slightly acidic to weakly alkaline solution (pH 5–8) of the UV sensitive biopesticide. The preferred UV protectant is a material which effectively absorbs UV light in the 290–400 nm range and which has functional groups which can complex with protonated proteins. A mineral acid such as hydrochloric acid (HCL), sulfuric acid ($H_2SO_4$), nitric acid ($HNO_3$), phosphoric acid ($H_3PO_4$) or acetic acid ($CH_3COOH$) is then added to adjust the pH of the resulting mixture to 3–4. Under these conditions cationic salts of the amino acid groups of the proteinacious toxins are generated. These cationic groups react through attractive forces with the anionic sulfonic acid groups of the UV absorber—the result of which is the formation of a complex of the UV protectant with the proteinacious materials (i.e. toxins or toxin carriers) in the biopesticide as shown in Scheme 1.

SCHEME 1

$$LIGNIN-SO_3^-Na^+ + H_3^+N-CHRCO_2HCl^- \xrightarrow{-NaCl}$$

$$LIGNIN-SO_3^-H_3^+N-CHRCO_2H$$

By use of an excess of UV protectant, enough anionic sulfonic acid groups are present to ensure complete complexation of all available cationic site in the protein and protection is maximized.

EXAMPLE I

This example illustrates the formation of a conventional lignosulfonate UV protectant/biopesticide toxin complex. Five grams of off-white $B_t$ (*Bacillus thuringieusis*) actives in water (pH 5.5) were mixed with one gram of Marasperse B-3D, a high molecular weight lignosulfonate product from LignoTech USA. The pH of the mixture was adjusted to 4.0 by dropwise addition of 0.1N HCl. The solids in the mixture were isolated by centrifugation and washed with 20 ml aliquats of 0.05M potassium biphthalate until a colorless flitrate was obtained. The brown color of the final solids obtained after washing indicated a stable $B_t$ toxin/Marasperse B-3D complex had been formed. Addition of 0.5N NaOH to a resuspension of the complex (pH 8.0) followed by repeated washing with distilled water gave an off-white colored product indicating that complex formation was reversible.

EXAMPLE II

This example illustrates the formation of a modified lignosulfonate UV protectant/biopesticide toxin complex. Five grams of off-white $B_t$ actives in water (pH 5.5) were mixed with 0.5 gram of an azo-lignosulfonate prepared from Marasperse CBOS-6 and p-aminobenzoic acid using the methods described in U.S. Pat. No. 4,846,888. The pH of the mixture was adjusted to 4.0 by dropwise addition of 0.1N HCl. The solids in the mixture were isolated by centrifugation and washed with 20 ml aliquats of distilled water until a colorless flitrate was obtained. The bright orange-brown color of the final solids obtained after washing indicated a stable $B_t$ toxin/Marasperse B-3D complex had been formed. Addition of 0.5N NaOH to a resuspension of the complex (pH 8.0) followed by repeated washing with distilled water gave an off-white colored product indicating that complex formation was reversible.

EXAMPLE III

Example III is another example of the formation of a modified lignosulfonate UV protectant/biopesticide toxin complex. Two hundred grams of off-white baculovirus in water (pH 6.0) were mixed with 10 grams of a highly purified and oxidized lignosulfonate. The pH of the mixture was adjusted to 4.0 by dropwise addition of 35% $H_2SO_4$. The solids in the mixture were isolated by centrifugation and washed with 200 ml aliquats of distilled water until a colorless filtrate was obtained. The dark brown color of the final solids obtained after washing indicated a stable complex between the Marasperse CBA-1 and the protein inclusion bodies housing the virus had been formed. Addition of 0.5N NaOH to a resuspension of the complex (pH 8.0) followed by repeated washing with distilled water gave an off-white colored product indicating that complex formation was reversible.

EXAMPLE IV

This example further illustrates the formation of a modified lignosulfonate UV protectant/biopesticide toxin complex. Fifty grams of DiPel, a $B_t$ product from Abbott Labs, was dissolved in 150 grams of water (pH 5.0). About 2.50 grams of Marasperse CBA-1 which is a highly purified and oxidized lignosulfonate was added to the mixture, and the pH of which was adjusted to 4.0 by dropwise addition of 35% $H_2SO_4$. The solids in the mixture were isolated by centrifugation and washed with 200 ml aliquats of distilled water until a colorless flitrate was obtained. The dark brown color of the final solids obtained after washing indicated a stable $B_t$ toxin/Marasperse B-3D complex had been formed. Addition of 0.5N NaOH to a resuspension of the complex (pH 8.0) followed by repeated washing with distilled water gave an off-white colored product indicating that complex formation was reversible.

EXAMPLE V

This example illustrates the UV protection imparted by the invention. DiPel reacted with a highly purified and oxidized lignosulfonate as described in Example IV was field tested against 10 10 unprotected DiPel for control of yellow strip armyworm (*Spodoptera ornitogalli*) damage in tomato plants. At the dosage tested (i.e. 1 kg/ha), both products performed equivalenfiy in terms of fruit damage, but the UV-protected DiPel maintained activity approximately 7 days longer than unprotected DiPel.

While the invention has been described herein by references to certain materials, procedures and examples, it is understood that it is not restricted to the particular materials, combination or materials and procedures selected for that purpose. Those skilled in the art should appreciate the numerous variations implied herein.

What is claimed is:

1. A method for improving the ultra-violet light and heat resistance of a biopesticide comprising reacting a proteinacious component of said biopesticide with an ultra-violet protectant to form a UV protectant-protein complex that decomposes in an alkaline environment, wherein the ultra-violet protectant is selected from the group consisting of a lignosulfonate, a sulfonated lignite, a sulfonated tannin, a napthalene sulfonate, a condensed napthalene sulfonate, and an azo-lignosulfonate.

2. The method of claim 1 wherein said biopesticide is a proteinacious insecticidal toxin, and said complex is formed directly with said toxin.

3. The method of claim 1 wherein said biopesticide is an insecticidal toxin carried in a protein matrix, and said complex is formed with said matrix.

4. The method of claim 1 wherein said biologically derived pesticide is a virus.

5. The method of claim 4 wherein said virus is a nuclear polyhedrosis virus.

6. The method of claim 5 wherein said nuclear polyhedrosis virus is selected from *Hellothis zea, H. virescens, Lymantrai dispar, Orgai pseudotsugata, Neodiprion sertifer*, and *Autographa californica*.

7. The method of claim 1 wherein said biologically derived pesticide is a bacterium.

8. The method of claim 7 wherein said bacterium is selected from *Bacillus thuringiensis, Bacillus sphaericus, Bacillus popilliae*, and *Bacillus cereus*.

9. The method of claim 1 wherein said biologically derived pesticide is a nematode.

10. The method of claim 9 where said nematode is selected from *Neoaptectana carpocapsae, Octomyomermis muspratti, Steinemema carpocapsae* and *Romanomermis culiciuora*.

11. The method of claim 1 wherein said biologically derived pesticide is a fungus.

12. The method of claim 11 wherein said fungus is selected from *Verticittum lecanii* and Entomophathora genus.

13. The method of claim 1 wherein the ultra-violet protectant is modified to have increased ultra-violet absorbance in the 290–400 nm range.

14. A process for preparing an ultra-violet light and heat resistant biopesticide, comprising the steps of:

(a) preparing a mixture of a biopesticide and an ultra-violet protectant in a neutral or slightly alkaline solution having a pH of about 5 to 8, wherein the ultra-vilet protectant is selected from the group consisting of a lignosulfonate, a sulfonated lignite, a sulfonated tannin, a napthalene sulfonate, a condensed napthalene sulfonate, and an azo-lignosulfonate;

(b) acidifying the resultant mixture to a pH of about 3.5 to 4.5 until a complex of a proteinacious component of said biopesticide and the ultra-violet protectant is formed; and (c) recovering the complex.

15. The process of claim 14 wherein the step of acidifying the resultant mixture comprises adding an acid to said mixture.

16. The process of claim 15 wherein said acid is a mineral acid selected from hydrochloric acid, sulfuric acid, nitric acid, phosphoric acid and acetic acid.

17. The process of claim 14 wherein the step of recovering the complex comprises spray drying the resultant mixture.

18. The process of claim 14 further including the step of adding a buffer to the resultant mixture to maintain the desired pH.

19. The process of claim 18 wherein the buffer is potassium acid phthalate.

* * * * *

UNITED STATES PATENT AND TRADEMARK OFFICE
CERTIFICATE OF CORRECTION

PATENT NO. : 5,529,772
DATED : June 25, 1996
INVENTOR(S) : Stuart E. Lebo, Jr.

It is certified that error appears in the above-indentified patent and that said Letters Patent is hereby corrected as shown below:

IN THE CLAIMS:

CLAIM 6
Col. 7, line 9

Delete the "Hellothis" and substitute therefor ---Heliothis---.

CLAIM 10
Col. 7, line 20

Delete "Neoaptectana" and substitute therefor ---Neoaplectana---.

CLAIM 12
Col. 7, line 26

Delete "Verticittum" and substitute therefor ---Verticillum---.

CLAIM 14
Col. 8, line 5

Delete "ultra-vilet" and substitute therefor ---ultra-violet---.

Signed and Sealed this

Seventh Day of January, 1997

Attest:

BRUCE LEHMAN

*Attesting Officer*     *Commissioner of Patents and Trademarks*